(12) United States Patent
Regnier et al.

(10) Patent No.: US 11,602,637 B2
(45) Date of Patent: Mar. 14, 2023

(54) AUTONOMOUS IMPLANTABLE AND REMOVABLE CARDIAC CAPSULE WITH A SWIVELING HEAD AND A TORQUE LIMITER

(71) Applicant: CAIRDAC, Antony (FR)

(72) Inventors: Willy Regnier, Longjumeau (FR); An Nguyen-Dinh, La Riche (FR)

(73) Assignee: CAIRDAC, Anthony (FR)

( * ) Notice: Subject to any disclaimer, the term of this patent is extended or adjusted under 35 U.S.C. 154(b) by 15 days.

(21) Appl. No.: 17/528,883

(22) Filed: Nov. 17, 2021

(65) Prior Publication Data
US 2022/0288402 A1    Sep. 15, 2022

(30) Foreign Application Priority Data
Mar. 15, 2021   (EP) .................................... 21315036

(51) Int. Cl.
*A61N 1/05*   (2006.01)
*A61N 1/375*  (2006.01)
*A61N 1/39*   (2006.01)

(52) U.S. Cl.
CPC ....... *A61N 1/37518* (2017.08); *A61N 1/0573* (2013.01); *A61N 1/3756* (2013.01); *A61N 1/3956* (2013.01)

(58) Field of Classification Search
CPC . A61N 1/0573; A61N 1/37518; A61N 1/3756
See application file for complete search history.

(56) References Cited

U.S. PATENT DOCUMENTS

| | | | | |
|---|---|---|---|---|
| 9,889,295 | B2* | 2/2018 | Ollivier | A61N 1/375 |
| 9,974,948 | B2* | 5/2018 | Ollivier | A61N 1/37205 |
| 10,881,868 | B2* | 1/2021 | Ollivier | A61N 1/3756 |
| 11,197,997 | B2* | 12/2021 | Regnier | A61B 5/283 |
| 11,229,799 | B2* | 1/2022 | Nguyen-Dinh | A61N 1/37512 |
| 2009/0171408 | A1 | 7/2009 | Solem | |

(Continued)

FOREIGN PATENT DOCUMENTS

WO    2018122244 A1    7/2018

OTHER PUBLICATIONS

European Search Report for European Application No. 21315036.0 dated Aug. 31, 2021.

*Primary Examiner* — Eric D. Bertram
(74) *Attorney, Agent, or Firm* — Haverstock & Owens, A Law Corporation

(57) ABSTRACT

The capsule comprises a tubular body and a front-end unit with an helical screw for anchoring the capsule to a wall of a patient's organ. The front-end unit is mobile in relative axial rotation with respect to the tubular body. A disengageable frictional coupling member allows this relative rotation when, for implantation, the tubular body receives an external rotational stress, and that until a predetermined limit torque triggering the disengagement. At explantation, this disengagement is prevented to allow a joint rotation of the tubular body and of the front-end unit and the unscrewing of the helical screw. It is provided for that purpose two conjugated plates facing each other, with flat surfaces such as circular sectors offset in opposite directions with respect to a radial reference plane, in such a way as to form steps providing an anti-disengagement abutment function.

14 Claims, 4 Drawing Sheets

(56) References Cited

U.S. PATENT DOCUMENTS

| | | | |
|---|---|---|---|
| 2014/0378991 A1* | 12/2014 | Ollivier | A61N 1/056 606/129 |
| 2014/0378992 A1* | 12/2014 | Ollivier | A61N 1/37205 606/129 |
| 2015/0306378 A1* | 10/2015 | Schmidt | A61N 1/37205 607/126 |
| 2015/0374976 A1 | 12/2015 | Regnier et al. | |
| 2017/0151429 A1 | 6/2017 | Regnier | |
| 2017/0340877 A1* | 11/2017 | Ollivier | A61N 1/3756 |
| 2020/0094048 A1* | 3/2020 | Regnier | A61B 5/283 |
| 2020/0164215 A1* | 5/2020 | Nguyen-Dinh | A61N 1/37518 |
| 2021/0085990 A1* | 3/2021 | Rickheim | A61M 25/0082 |
| 2022/0288402 A1* | 9/2022 | Regnier | A61B 5/6861 |

* cited by examiner

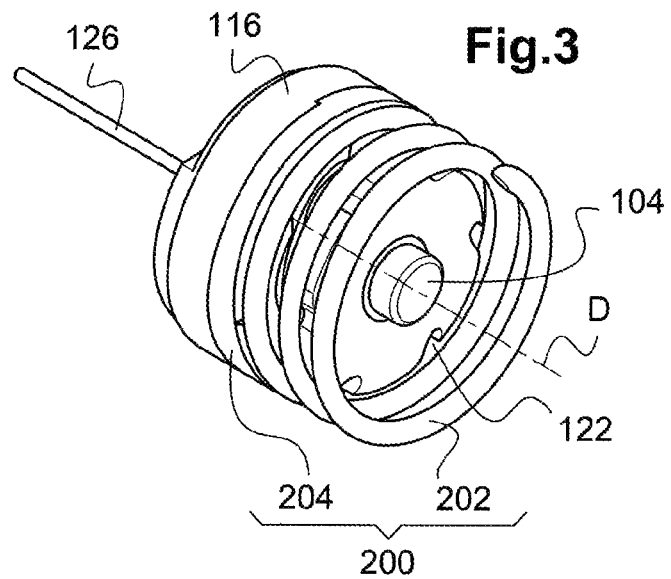
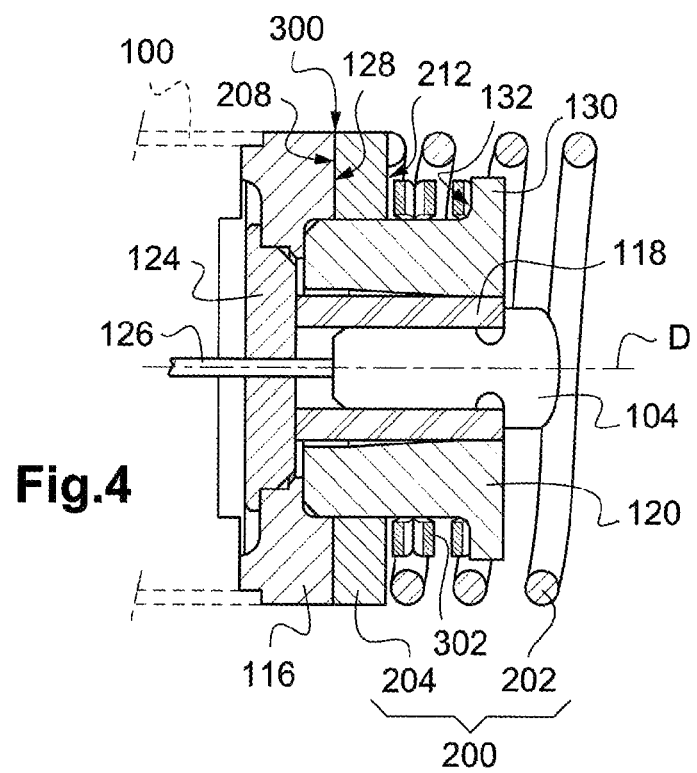

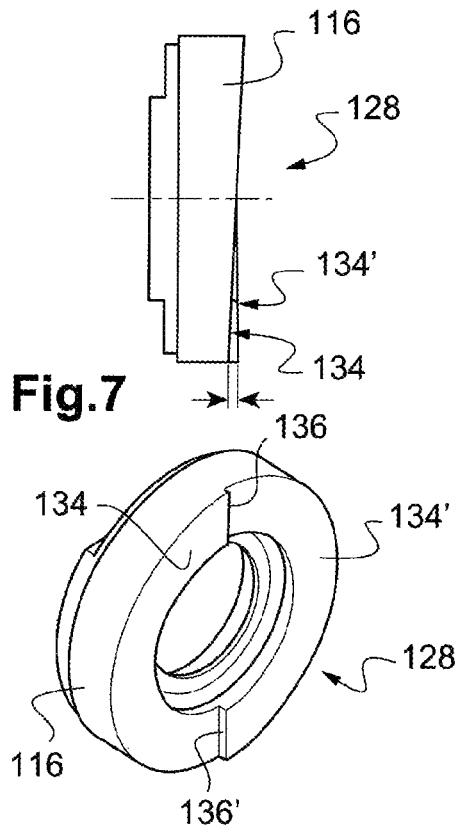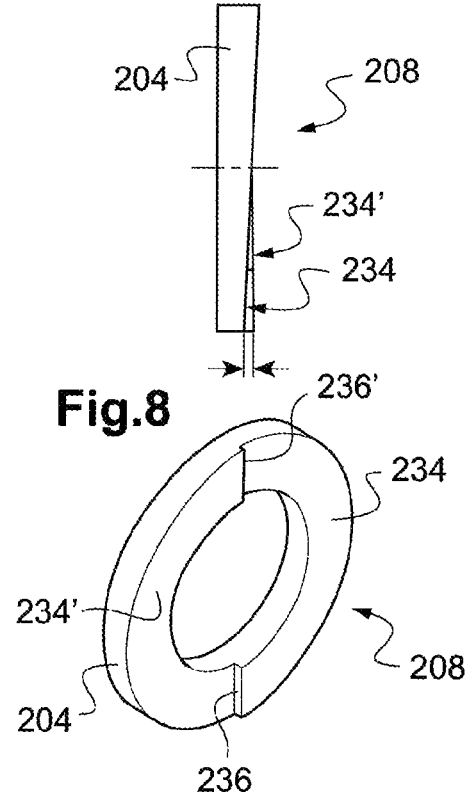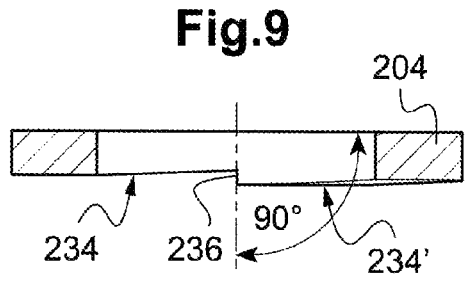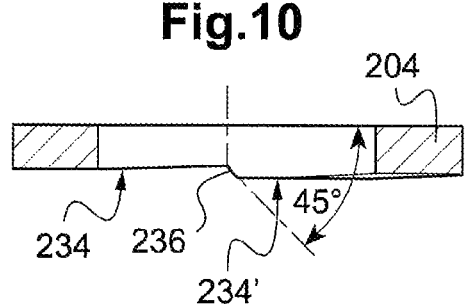

AUTONOMOUS IMPLANTABLE AND REMOVABLE CARDIAC CAPSULE WITH A SWIVELING HEAD AND A TORQUE LIMITER

BACKGROUND OF THE INVENTION

Field of the Invention

The invention relates to implantable medical devices, in particular devices of the autonomous implantable capsule type.

More particularly, the invention relates to such devices which are in the form of an autonomous capsule implanted in a heart chamber (ventricle, atrium or even arterial left heart chamber), hereinafter referred to as "autonomous capsule", "leadless capsule" or simply "capsule") (the autonomous character of the capsule being not in itself a necessary feature of the invention). These autonomous capsules are devoid of any physical connection to a main device, whether the latter is an implanted device (such as a stimulation pulse generator box) or a non-implanted device (external peripheral such as a programmer or a monitoring device for the remote follow-up of the patient), and are, for that reason, referred to as "leadless" capsules, to distinguish them from the electrodes or the sensors arranged at the distal end of a conventional lead, along the whole length of which run one or several conductors galvanically connecting the electrode or the sensor to a generator connected to an opposite, proximal end of the lead.

The invention is however not limited to a particular type of capsule, nor even of leadless implant, and it is applicable as well to many other types of implantable medical devices, whatever the operational purpose thereof, cardiac or other, for example capsules intended to diffuse in situ an active pharmacological agent.

In this case of cardiac application, the capsule continuously monitors the patient's rhythm and, if necessary, delivers to the heart pacing, resynchronization and/or defibrillation electrical pulses in case of rhythm disorders detected by the capsule. The capsule may be an epicardial capsule, fixed to the external wall of the heart, or an endocavitary capsule, fixed to the internal wall of a ventricular or atrial chamber, or also a capsule fixed to a vessel wall near the myocardium.

The capsules comprise various electronic circuits, sensors, etc., as well as wireless communication transmitter/receiver means for remote exchange of data, the whole being integrated in a body of very small size able to be implanted in sites of difficult access or leaving small room, such as the ventricle apex, the internal wall of the atrium, etc.

US 2009/0171408 A1 (Solem), US 2015/374976 A1 (Regnier), US 2017/0151429 A1 (Regnier) and WO 2018/122244 A1 (Regnier) disclose various examples of such intracardiac leadless capsules.

Description of the Related Art

The invention more particularly relates to problems linked to the implantation in situ and the explantation of such capsules when the latter are provided, at their distal end, with an anchoring member adapted to enter the tissues of a body wall at the chosen implantation site.

A typical example of such an anchoring member comprises a protruding helical screw axially extending the capsule body and intended to enter the heart tissue by being screwed thereinto at the implantation site.

In the case of endocavitary capsules (i.e. capsules to be fixed to the inner wall of a ventricular or atrial chamber, by opposition to epicardial capsules, fixed to the outer wall of the heart), the "delivery", i.e. the positioning to the implantation site, consists in mounting the capsule at the end of a guide catheter of an implantation accessory, then to make it move along the peripheral venous network and to orientate it up to the chosen site, for example the apex of the right ventricular chamber. Once the implantation site reached, the practitioner imparts to the capsule, through the guide catheter, combined movements of axial translation (to make the capsule move forward then to exert a pressure against the heart wall) and of rotation of the capsule about itself (to operate the screwing of the anchoring member into the thickness of the heart wall). Once the capsule firmly anchored in the heart wall, the operator proceeds to the "release" of the capsule, i.e. its separation from the implantation accessory, so that the capsule then become fully autonomous.

To avoid, at the time of fixing the capsule into the wall, any risk of coring of the tissues due to an excessive screwing, it is imperative, at the time of screwing the anchoring member, not to exceed a limit torque (hereinafter "coring torque") beyond which the anchoring screw would be liable to locally tear the tissues under the effect of a rotation of the screw without forward move of the latter, until causing a laceration of the tissues and, in the extreme, a perforation of the wall with a risk of tamponade (in particular, in the case of an implantation into a thin wall such as the interatrial septum or the apical area of the right ventricle).

US 2020/094048 A1 (Regnier) discloses a solution implementing a torque limitation system intrinsic to the capsule, more precisely a system comprising a head integral with the anchoring screw and rotatable with respect to the capsule body. Between the capsule body and the mobile head is arranged a disengageable frictional coupling mechanism preventing the rotation of the mobile head with respect to the capsule body as long as the reaction torque exerted by the anchoring screw is lower that a predetermined threshold, and allowing this rotation as soon as the reaction torque exceeds the predetermined threshold. This system for disengaging the mobile head, and hence the anchoring screw, from the capsule body driven by the guide catheter, allows for tissue preservation at the implantation site while avoiding any laceration or coring, whereby ensuring the best conditions of implantation for the capsule.

The present invention is concerned with another step of the capsule handling, which is the explantation, i.e. the removal of the capsule from the implantation site, by detaching it from the wall to which it had been anchored.

The aim of this is to unscrew the anchoring screw by imparting to the capsule body a rotation in the unscrewing direction (i.e. counterclockwise), opposite to that exerted for the implantation (in the screwing direction, i.e. clockwise). The unscrewing torque is applied to the capsule body by a catheter that has been brought up to the chamber in which the capsule is implanted; the distal part of the catheter comprises a means for gripping the rear portion of the capsule (proximal part, i.e. that which is opposite to the heart wall) in order to couple to the latter and to be able to rotate the capsule body, and consequently, the front-end unit and the anchoring screw.

If the capsule has been recently installed, or if the explantation consists simply, during implantation, in removing the capsule from a first site to try to find a better one, this procedure does not pose any particular difficulty.

On the other hand, clinical studies have shown that, especially after a long period of implantation, fibrosis develops at the implantation site, around the anchoring screw; the latter may also be more or less trapped among the trabeculations at the bottom of the ventricle when such a site is chosen.

It is then necessary that the friction torque between the two conjugated elements of the coupling mechanism (i.e. between the mobile front-end unit and the capsule body) be sufficient to transmit to the screw the unscrewing torque exerted from the rear of the capsule body. In particular, if the site is fibrosed, the capsule body might turn loosely, with the screw remaining stationary in place.

In the system disclosed by above-mentioned US 2020/094048 A1, the disengageable coupling mechanism with a torque limiter is effective at the time of the implantation in order to control the transmission of the torque to the heart muscle during the screwing of the capsule. But at the time of the explantation, since the disengagement torque is indiscriminately effective in both directions of rotation (screwing and unscrewing), then the frictional coupling mechanism might be in a permanently disengaged state due to a high reaction torque exerted by the adhesion of the anchoring screw to the heart wall.

The object of the present invention is to solve this problem of a friction of the disengageable coupling mechanism which is insufficient to transmit an unscrewing torque during an operation of explantation of an already-implanted capsule.

BRIEF SUMMARY OF THE INVENTION

The basic idea of the invention is to provide a disengageable frictional coupling mechanism that applies in a differentiated manner in both directions of rotation (screwing/unscrewing), in such a way as to cancel the disengagement effect only in the unscrewing direction, without changing the operation of the disengageable coupling in the screwing direction.

For that purpose, the invention proposes an implantable autonomous capsule of the type described in above-mentioned US 2020/094048 A1, namely comprising: a tubular body housing a set of functional elements of the capsule; at a front, distal end of the capsule, a front-end unit comprising a helical-screw anchoring member for anchoring the capsule to a wall of a patient's organ; a disengageable frictional coupling, arranged at said distal end of the capsule between the front-end unit and the tubular body; and, at an opposite, proximal end of the capsule, means for connecting the capsule to an implantation/explantation accessory. The front-end unit and the helical screw are mobile as a whole in relative axial rotation with respect to the tubular body, and the disengageable frictional coupling is arranged in such a way as, when an external axial rotational stress is applied to the tubular body at the proximal end in a first direction corresponding to a screwing direction of the helical screw: to prevent the relative axial rotation as long as a reaction torque, exerted by the helical screw during the screwing into the wall of the patient's organ, is lower than a first predetermined threshold torque, and to allow the relative axial rotation as soon as the reaction torque exceeds the first predetermined threshold torque.

Characteristically of the invention, the disengageable frictional coupling further includes a one-way unscrewing blocking mechanism. This one-way blocking mechanism is arranged in such a way as, when an external axial rotational stress is applied to the tubular body at the proximal end in a second direction, opposite to the first direction and corresponding to an unscrewing direction of the helical screw: to prevent a disengagement of the coupling mechanism, by forbidding the relative axial rotation against a resistive torque exerted on the front-end unit by the helical screw during an unscrewing, whereby allowing a joint rotation of the tubular body and the front-end unit; and to be without effect in the screwing direction.

In a preferential, advantageous embodiment, the disengageable frictional coupling comprises two conjugated plates facing each other, with i) a first plate extending radially and integral with the tubular body and ii) a second plate extending radially and integral with the front-end unit, the one-way blocking mechanism is formed by the two conjugated plates that have respective surface configurations forming an anti-return mechanism in such a was as, when the two plates are in mutual contact, to allow the relative rotation of the two plates in the first direction and to prevent the relative rotation of the two plates in the second direction.

According to various advantageous implementations of this embodiment:
- the respective surface configurations facing each other and in contact with the two conjugated plates form a friction interface, and the disengageable coupling member comprises an elastically deformable element adapted to apply an axial force of compression of the two conjugated plates against each other;
- in the absence of an external rotational stress applied to the tubular body, the elastically deformable element applies at the friction interface a sufficient force to prevent the relative axial rotation as long as the reaction torque exerted by the helical screw during the screwing into the wall of the patient's organ remains lower than the first predetermined threshold torque, and to allow the relative axial rotation as soon as the reaction torque exceeds the first predetermined threshold torque;
- at least one of the first and second plate comprises a plurality of circular sectors offset in opposite directions with respect to a radial reference plane, with a step extending radially at each transition between adjacent circular sectors;
- in this later case, the steps can be substantially perpendicular to the surface of the circular sectors, or inclined by an angle lower than 90° with respect to the surface of the circular sectors, preferably inclined by an angle of 45°; the steps can have a height comprised between 3 and 7%, preferably a height of 5%, of the radius of the circular sectors;
- the circular sectors can be flat, and/or the first and the second plate can both comprise a plurality of circular sectors respectively forming symmetrical steps facing each other;
- as an alternative, the first and second plate can comprise a plurality of conjugated bosses and/or recesses forming the anti-return mechanism.

In an advantageous improvement, the one-way blocking mechanism is further arranged in such a way as, when the external axial rotational stress in the second direction is applied to the tubular body: to prevent the relative axial rotation as long as the reaction torque exerted on the front-end unit by the helical screw during the unscrewing remains lower than a second predetermined threshold torque, and to allow the relative axial rotation when the resistive torque exerted on the front-end unit by the helical screw during the unscrewing exceeds the second predetermined threshold torque.

BRIEF DESCRIPTION OF THE DRAWINGS

Various exemplary embodiments of the present invention will now be described with reference to the appended drawings, in which the same references denote identical or functionally similar elements throughout the figures.

FIG. 3 is a perspective overall view of the front-end unit according to the invention, located at the proximal end of a capsule such as that of FIG. 2.

FIG. 4 is a cross-sectional perspective view of the front-end unit of FIG. 3.

FIG. 7 is a front elevation and perspective view, in isolation, of the closing cap integral with the tubular body.

FIG. 8 is a rear elevation and perspective view, in isolation, of the support ring integral with the helical screw.

FIG. 9 is a cross-sectional view, along an axial plane, of the support ring of FIG. 8.

FIG. 10 is homologous to FIG. 9, for an alternative embodiment.

DETAILED DESCRIPTION OF A PREFERRED EMBODIMENT OF THE INVENTION

An exemplary embodiment of a capsule according to the invention will now be described.

Figure 1:
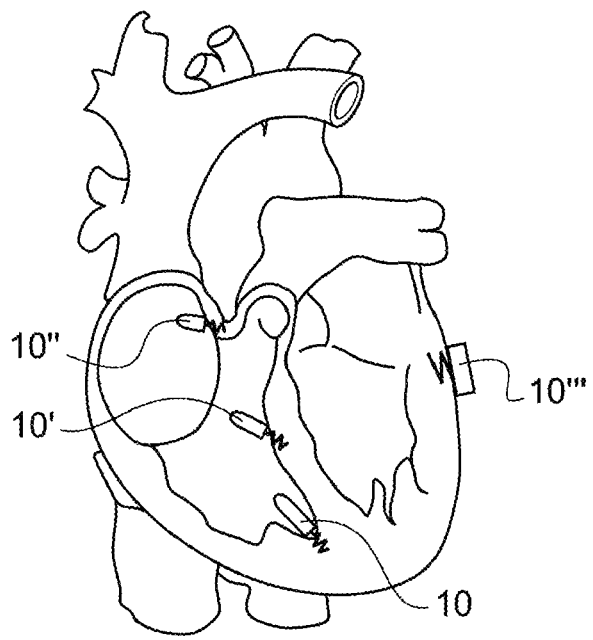
FIG. 1 illustrates medical devices of the leadless capsule type in their environment, with various examples of implantation sites in, on, or near the heart of a patient.

In FIG. 1 are shown various possibilities of implantation sites for a device of the leadless type, in an application to cardiac pacing. Hence, capsule 10 is implanted inside a myocardium chamber (endocavitary implant), for example at the apex of the right ventricle. As an alternative, the capsule may also be implanted on the right interventricular septum, as in 10', or on an atrial wall, as in 10". The device may also be an epicardial capsule placed in an external region of the myocardium, as in 10'''.

In each case, the leadless capsule is fixed to the heart wall by means of a protruding anchoring system such as a helical screw entering the heart tissue for holding it to the implantation site.

Figure 2:
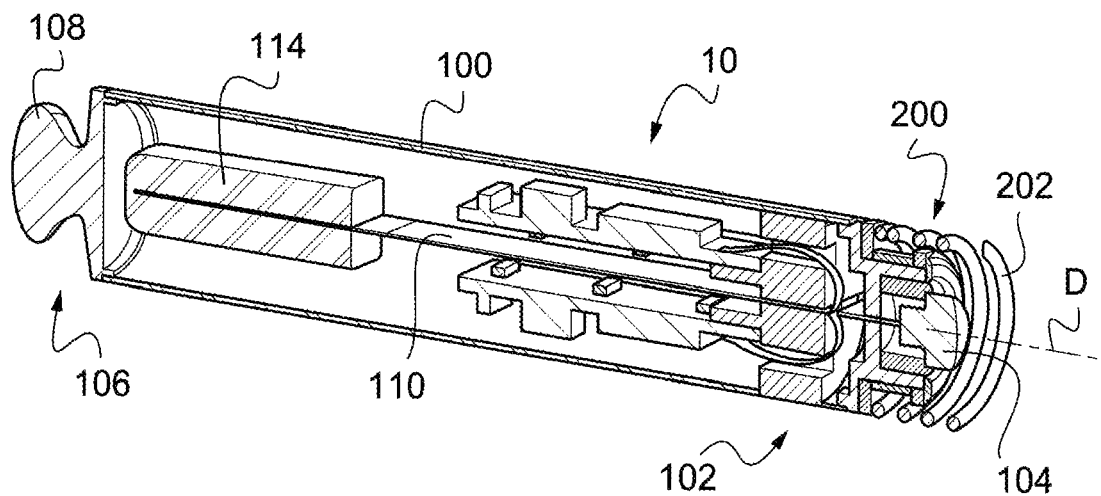
FIG. 2 is a longitudinal cross-sectional perspective view of an example of leadless capsule, showing the mechanical configuration of the different elements located inside the tubular envelope of the capsule.

FIG. 2 is a longitudinal cross-sectional perspective view of an example of leadless capsule showing the mechanical configuration of the different elements located inside the tubular envelope of the capsule.

The leadless capsule 10 is in the external form of an implant comprising a cylindrical elongated tubular body 100 enclosing the various electronic and power supply circuits of the capsule as well as, in the illustrated (non-limitative) example, an energy harvester with a pendular unit. The typical size of such a capsule is a diameter of the order of 6 mm for a length of about 25-40 mm.

The elongated tubular body 100 is closed at its front (distal) end 102 by a front-end unit 200 carrying a helical screw 202 for the anchoring of the capsule to a wall of a heart chamber, as illustrated hereinabove with respect to FIG. 1. A sensing/pacing electrode 104, in contact with the heart tissue at the implantation site, collects the cardiac depolarization potential and/or applies pacing pulses.

The opposite, rear (proximal) end 106 of tubular body 100 of capsule 10 has an atraumatic rounded shape and is provided with suitable means 108, such as a gripping shape for the connection to a guide catheter or another implantation accessory usable at the time of capsule implantation or explantation. These means allow the practitioner, by a controlled action of combined rotation and translation of the guide catheter, to guide the capsule towards the implantation site and to secure it thereto by screwing anchoring element 202 into the wall.

During explantation, the reverse operation is implemented: the practitioner exerts, by means of the guide catheter, a screwing torque on the gripping shape at the proximal part of the capsule, this torque being transmitted to front-end unit 200 and to helical screw 202 to allow the unscrewing of the unit and the separation of the capsule from the heart wall.

Capsule 10 is advantageously provided with an energy harvesting module comprising an inertial pendular unit that oscillates, inside the capsule, following the various external stresses to which the capsule is subjected (movements of the wall to which the capsule is anchored, blood flow rate variations in the medium surrounding the implant, producing oscillations of the implant at the heartbeat rhythm, and/or various vibrations transmitted by the heart tissues). This pendular unit may in particular be of the mass-spring type, with a piezoelectric beam 110 clamped at one of its ends, and whose opposite, free end is coupled to a mobile inertial mass 114.

FIGS. 3 and 4 illustrate, in isolation, capsule front-end unit 200 mounted at the distal end of capsule tubular body 100, with electrode 104 intended to bear against the tissue surface at the implantation site and helical screw 202 intended to enter this tissue for anchoring the capsule to the implantation site.

Screw 202 is rotationally integral with a support ring 204, the screw being for example welded to this support ring, the two elements being metallic, for example made of stainless steel, such as 316L steel or a metal such as titanium, tantalum or a nickel-titanium alloy of the nitinol type.

(It will be noted incidentally that all the elements integral with tubular body 100 will be denoted by a numerical reference of the type 1nn, whereas all those which are integral with front-end unit 200 will be denoted by a numerical reference of the type 2nn).

Tubular body 100 is ended, opposite support ring 204, by a closing cap 116 of substantially flat shape and against which bears support ring 204. Closing cap 116, just as capsule tubular body 100, are metallic element, for example made of titanium or stainless steel, such as 316L steel, or also a nickel-titanium alloy of the nitinol type, both parts 100 and 116 being for example welded to each other.

Front-end unit 200, hence comprising anchoring screw 202 with its support ring 204, has, with respect to tubular body 100 and its closing cap 116 thereof, an axial rotational degree of freedom (i.e. about central axis D).

Tubular body 100 as well as the elements with which it is integral, on the one hand, and front-end unit 200, on the other hand, are coupled to each other by disengageable frictional means, which can in particular be of a type as described in above-mentioned US 2020/094048 A1. These disengageable means are adapted to provide a torque limiter function between the tubular body (that receives an external stress at the time of implantation via the implantation tool handled by the practitioner) and the anchoring screw (that enters the tissue, and for which it is essential to avoid any coring effect).

The torque limiter mechanism allows, when the tubular body is rotationally stressed in the screwing direction (CW direction, cf. FIG. 6) and hence applies to the anchoring screw a corresponding torque that allows the latter to enter the tissue, the transmission of this driving torque as long as the latter is lower than a predetermined threshold torque (chosen to be lower than the coring torque) and, if the driving torque exceeds this threshold, it prevents the coring, either by limiting this torque (which will continue to be transmitted from the tubular body to the front-end unit), or by fully disengaging the front-end unit of the tubular body (hence putting a end to the driving torque transmission). The predetermined threshold torque that triggers the disconnection of the front-end unit from the tubular body is typically lower than 1 N·cm, to avoid any risk of coring by the helical screw at the time of implantation. Concretely, the reaction torque increases relatively abruptly when the capsule front face (herein electrode 104) touches the heart tissue surface, then exerting to the anchoring screw an axial reaction force that, in the absence of disengagement action or torque limitation, would be liable to produce a coring.

If it is desired to explant the capsule, a rotation torque exerted in the reverse direction (CCW direction, cf. FIG. 6) on the tubular body will allow transmitting the unscrewing movement to the helical screw and hence to progressively detach the capsule from the wall.

Tubular body 100 and its closing cap 116 form with electrode 104 an integral unit carried by an electrode support sleeve 118 made of an electrically isolating material, for example a polyurethane thermoplastic polymer of the Tecothane® type or a polymer of the PET (polyethylene terephthalate) or PEEK (polyetheretherketone) type, or another injectable plastic material. Electrode 104 is connected to the electronic circuits located inside tubular body 100 by a conductor 126 passing through cap 116 and isolated from the latter by a feedthrough 124.

Figure 5:
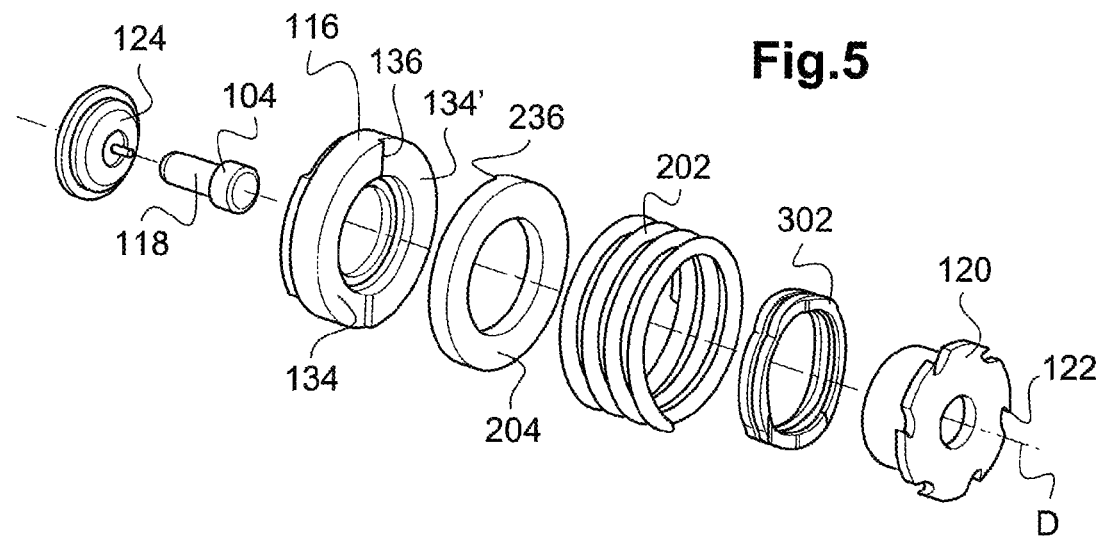
FIG. 5 is an exploded perspective view of the different elements constituting the unit of FIG. 4.

Isolating sleeve 118 is housed at the center of a metal crown 120, welded to the proximal side of closing cap 116. As can be seen in FIGS. 3 and 5, this crown 120 can be advantageously provided with protruding teeth 122 oriented in a circumferential direction opposite to the screwing direction and reinforcing the holding of the capsule to the heart tissue after the installation. The matter is to ensure that the capsule can be separated from the heart wall only by the voluntary intervention of a practitioner and following a predetermined procedure, but in no way due to an accidental unscrewing resulting for example from myocardium repeated movements or from tissue modification at the implantation site over time. Teeth 122 form as many anchoring points distributed over the endothelium, making the capsule non-removable in the absence of external explantation operation.

As regards front-end unit 200, which is mobile in rotation with respect to the just-described various elements 100 to 122, this unit comprises support ring 204, integral with helical screw 202 and having, on the proximal side, a bearing surface 208 directed towards a counterpart surface 128 of closing cap 116, with which it is in contact. These two surfaces 128 and 208, which are both metallic, form a first interface 300 with a mutual frictional effect.

On the distal side, surface 212 of support ring 204 bears against an annular spring 302, itself bearing, on the distal side, against a surface 132 formed by a shoulder 130 of crown 120, this surface 132 substantially extending in a radial plane and being directed in the proximal direction. Spring 302 is hence axially caught between support ring 204 (surface 212) and crown 120 (surface 132). This spring 302 exerts that way to support ring 204 an axial force towards tubular body 100, this force resulting in a frictional effect at interface 300 between closing cap 116 (surface 128) and support ring 204 (surface 208).

Figure 6:
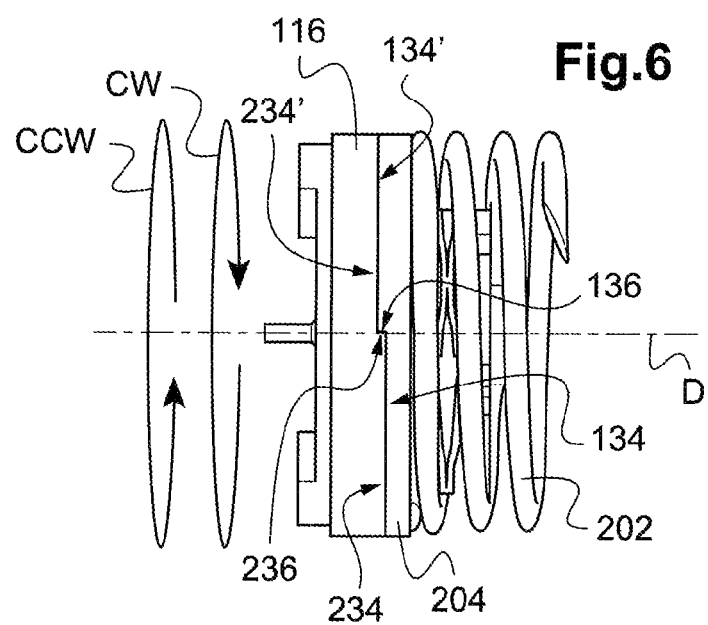
FIG. 6 is an elevation view, in an assembled configuration, of the front-end unit of FIGS. 4 and 5 explaining the two possible directions of rotation of the mobile elements.

This frictional coupling mechanism between closing cap 116, and thus tubular body 100, on the one hand, and support ring 204, and thus helical screw 202, on the other hand, allows, at the time of implantation, limiting the torque transmitted by tubular body 100 (driven in the CW screwing direction, which is the clockwise direction in FIG. 6) to anchoring screw 202 and hence obtaining the desired anti-coring torque limiter effect.

It will also be noted that, after having anchored the capsule into the wall, it is still possible to axially redirect the tubular body without exerting a rotary action to the screw, hence without risk of over-screwing liable cause a coring. This faculty may turn out to be interesting in the case of a capsule provided with an energy harvester such as that illustrated in FIG. 2, with a pendular unit provided with an inertial mass and a flexible beam; with this configuration, the energy harvesting may vary as a function of the orientation in space of the bending direction in the beam with respect to the heart wall, in such a way that it may be advantageous to optimize the energy conversion by rotating the capsule body up to find the position that maximizes this conversion.

For spring 300, it is advantageous to choose a corrugated spring that has for advantage a very high compactness, which is compatible with the requirements of extreme miniaturization of the leadless capsules. The advantage of such a corrugated spring is the axial space saving allowed, typically 50% with respect to a conventional helical wire spring. Other types of functionally similar springs or elements can however be used, such as: spacer made of flexible material, for example silicon, helical compression spring, leaf spring, deformable plastic ring, etc., the important point being that this element can generate between surfaces 208 and 128, at interface 300, a sufficient friction to limit the torque to the chosen predetermined value, while maintaining the angular orientation of tubular body 100 with respect to front-end unit 200 in the absence of torque applied from the outside of tubular body 100.

Characteristically of the present invention, conjugated surfaces 108 (of support ring 204) and 128 (of closing cap 116) include a mechanism operating during an explantation operation, in addition to the just-described frictional mechanism that makes it possible to avoid an anti-coring effect during the implantation.

This mechanism according to the invention intervenes when the tubular body is subjected by a practitioner, by means of a catheter coupled to the tubular body, to a rotation in the counterclockwise direction (CCW direction in FIG. 6) to unscrew the helical screw 202 in order to detach the capsule from the implantation site to which it is anchored.

With the only just-described torque-limiter frictional mechanism, if an unscrewing torque higher than the limit torque allowed at interface 300 (limit torque defined by the pressure of spring 302) is exerted, tubular body 100 continues to rotate but without this rotation is transmitted to helical screw 202. This situation can occur in particular when a fibrosis has developed over time at the implantation site, said fibrosis strongly increasing the adhesion of the screw to the heart tissue and increasing that way the torque required to unscrew helical screw 202. Moreover, the possible presence of hooking teeth 122 on crown 120 increases the force that has to be exerted during the unscrewing, insofar as the sharp edges of these teeth will tend to penetrate into the tissues during the unscrewing. To address this risk and prevent the disengagement of the coupling mechanism during an unscrewing operation, it is provided, according to the invention, a mechanism for blocking the mutual rotation of closing cap 116 and support ring 204, this mechanism being a one-way mechanism, forbidding the disengagement in the unscrewing direction but being without effect in the screwing direction (that is to say that, in the screwing direction, the two counterpart parts 116 and 124 are subjected to a friction contact, calibrated by the pressure of spring 302, hence with a possibility of mutual rotation when the reaction torque of helical screw 202 exceeds the predetermined threshold avoiding any coring).

In the embodiment illustrated in FIGS. 5 to 10, this one-way mechanism is made by giving closing cap surface 128 the shape of an annular plate with a plurality of circular sectors, in the example illustrated two annular circular sectors 134, 134', slightly offset in opposite directions relative to each other with respect to a radial reference plane, in such a way as to form at the connection between these two circular sectors 134, 134' two steps 136, 136' (see in particular FIG. 7) oriented radially.

Comparably, surface 208 that is opposite the proximal face of support ring 204 is made as an annular plate with two annular circular sectors 234, 234' slightly offset in opposite directions relative to each other with respect to a radial reference plane, in such a way as to form at the connection between these two circular sectors 234, 234' two steps 236, 236' oriented radially.

Steps 136, 136' and 236, 236' have typically a height between 3 and 7%, for example 5%, of the radius of the respective surface 128, 208, i.e. a step height of about 0.2 mm for a radius of 3.8 mm.

The surfaces of the annular circular sectors 134, 134' and 234, 234' are chosen in such a way that the two counterpart parts 116 and 204 remain in mutual contact with each other (surface 134 against surface 234 and surface 134' against surface 234') in such a way as to maintain a frictional coupling in the screwing direction.

On the other hand, in the unscrewing direction, closing cap steps 136, 136' will come into abutment against the counterpart steps 236, 236' of support ring 204, which will have for effect to neutralize the frictional coupling and to impart an axial rotation to support ring 204, and hence to helical screw 202, under the effect of the rotation applied to tubular body 100, and hence to closing cap 116 in contact with support ring 204.

The configuration of the illustrated example, with two flat and inclined annular circular half-sectors, is however not limitative of the invention. The number of sectors could be different (one, three, four, . . . ), and the sectors not necessary flat, as long as at least one radial step can be formed on at least one of the two parts 116 or 204 with, on the opposite conjugated part 204 or 116, a shape configuration allowing it to come into abutment with this(these) step(s), whether it is a step similar to that of the first part as in the illustrated example, or of another abutment shape such as boss, stud or shoulder, as long as the anti-return mechanism effect is obtained in the unscrewing direction while continuing to provide the frictional coupling in the screwing direction.

According to another, subsidiary and advantageous feature of the invention, the angle of step 136, 236, or of the equivalent abutment formation, can be modified to provide an additional torque limitation function, during the unscrewing.

Indeed, in the above description, it has always been considered that the one-way anti-disengagement mechanism operates regardless of the unscrewing torque applied to tubular body 100.

It can however be desirable to limit this torque to a relatively high limit value, in case of excessive reaction torque of the helical screw due to an excessive adhesion of the tissues, in particular due to a fibrosis developed over time. In this case, it is preferable not to try to explant the capsule using an excessive unscrewing torque, at the risk of tearing the tissues and to cause a perforation of the heart wall.

To address this risk, instead of providing for steps 136 and/or 236, as in the previous case, an angle of 90 degrees (as illustrated in FIG. 9) with respect to the planes of the corresponding faces 134, 134' and/or 234, 234', this angle is reduced, for example to 45 degrees (as illustrated in FIG. 10). With such a reduced angle, the unscrewing will remain possible until a certain limit torque, with an axial rotation uncoupling of parts 116, 204 by step jumping in case of excessive reaction torque of the helical screw (the limit torque being all the lower as the step inclination angle is far from the right angle). For the case mentioned hereinabove of an abutment of the boss or stud type, a comparable effect can be obtained by giving this abutment an inclined or rounded shape.

Another advantage of an angle lower than 90° lies in a protection against the risk of particle detachment when the limit disengagement torque is reached and the two parts 116, 204 are uncoupled from each other in axial rotation and slide on each other. Indeed, with an inclined step, the relative movement of these two parts is then progressive, and not abrupt, as with the jump of a step of 90 degrees.

The invention claimed is:

1. An implantable autonomous capsule, comprising:
    a tubular body housing a set of functional components of the capsule;
    at a front, distal end of the capsule, a front-end unit comprising a helical-screw anchoring member for anchoring the capsule to a wall of a patient's organ;
    a disengageable frictional coupling, arranged at said distal end of the capsule between the front-end unit and the tubular body; and
    at an opposite, proximal end of the capsule, means for connecting the capsule to an implantation/explantation accessory,
    wherein the front-end unit and the helical screw are mobile as a whole in relative axial rotation with respect to the tubular body,
    and wherein the disengageable frictional coupling is arranged in such a way as, when an external axial rotational stress is applied to the tubular body at the proximal end in a first direction corresponding to a screwing direction of the helical screw:
        to prevent the relative axial rotation as long as a reaction torque, exerted by the helical screw during the screwing into the wall of the patient's organ, is lower than a first predetermined threshold torque, and
        to allow the relative axial rotation as soon as the reaction torque exceeds the first predetermined threshold torque,
    wherein the disengageable frictional coupling further includes a one-way unscrewing blocking mechanism,
    said one-way blocking mechanism being arranged in such a way as, when an external axial rotational stress is applied to the tubular body at the proximal end in a second direction, opposite to the first direction and corresponding to an unscrewing direction of the helical screw:

to prevent a disengagement of the coupling mechanism, by forbidding the relative axial rotation against a resistive torque exerted on the front-end unit by the helical screw during an unscrewing, whereby allowing a joint rotation of the tubular body and the front-end unit; and to be without effect in the screwing direction.

2. The capsule of claim 1,
wherein the disengageable frictional coupling comprises two conjugated plates facing each other, with i) a first plate extending radially and integral with the tubular body and ii) a second plate extending radially and integral with the front-end unit,
and wherein the one-way blocking mechanism is formed by the two conjugated plates that have respective surface configurations forming an anti-return mechanism in such a was as, when the two plates are in mutual contact, to allow the relative rotation of the two plates in the first direction and to prevent the relative rotation of the two plates in the second direction.

3. The capsule of claim 2, wherein:
the respective surface configurations facing each other and in contact with the two conjugated plates form a friction interface; and
the disengageable coupling member comprises an elastically deformable element adapted to apply an axial force of compression of the two conjugated plates against each other.

4. The capsule of claim 3, wherein, in the absence of an external rotational stress applied to the tubular body, the elastically deformable element applies at the friction interface a sufficient force to prevent the relative axial rotation as long as the reaction torque exerted by the helical screw during the screwing into the wall of the patient's organ remains lower than the first predetermined threshold torque, and to allow the relative axial rotation as soon as the reaction torque exceeds the first predetermined threshold torque.

5. The capsule of claim 2, wherein at least one of the first and second plate comprises a plurality of circular sectors offset in opposite directions with respect to a radial reference plane, with a step extending radially at each transition between adjacent circular sectors.

6. The capsule of claim 5, wherein the steps are substantially perpendicular to the surface of the circular sectors.

7. The capsule of claim 5, wherein the steps are inclined by an angle lower than 90° with respect to the surface of the circular sectors.

8. The capsule of claim 7, wherein the steps are inclined by an angle of 45° with respect to the surface of the circular sectors.

9. The capsule of claim 5, wherein the circular sectors are flat sectors.

10. The capsule of claim 5, wherein the first and the second plate can both comprise a plurality of circular sectors respectively forming symmetrical steps facing each other.

11. The capsule of claim 5, wherein the steps have a height between 3 and 7% of the radius of the circular sectors.

12. The capsule of claim 11, wherein the steps have a height of 5% of the radius of the circular sectors.

13. The capsule of claim 2, wherein the first and the second plate comprise a plurality of conjugated bosses and/or recesses forming the anti-return mechanism.

14. The capsule of claim 1, wherein the one-way blocking mechanism is further arranged in such a way as, when the external axial rotational stress in the second direction is applied to the tubular body:
to prevent the relative axial rotation as long as the reaction torque exerted on the front-end unit by the helical screw during the unscrewing remains lower than a second predetermined threshold torque, and
to allow the relative axial rotation when the resistive torque exerted on the front-end unit by the helical screw during the unscrewing exceeds the second predetermined threshold torque.

* * * * *